(12) United States Patent
Laus et al.

(10) Patent No.: US 7,560,104 B2
(45) Date of Patent: Jul. 14, 2009

(54) COMPOSITIONS AND METHODS FOR ENHANCEMENT OF MAJOR HISTOCOMPATIBILITY COMPLEX CLASS I RESTRICTED ANTIGEN PRESENTATION

(75) Inventors: Reiner Laus, Bellevue, WA (US); Itzhak Hakim, Palo Alto, CA (US); Damir Vidović, Bellevue, WA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 11/455,031

(22) Filed: Jun. 16, 2006

(65) Prior Publication Data

US 2006/0292165 A1 Dec. 28, 2006

(51) Int. Cl.
*C12N 5/00* (2006.01)
*C12N 5/06* (2006.01)
*A61K 39/00* (2006.01)

(52) U.S. Cl. .............. 424/93.7; 424/93.71; 435/325
(58) Field of Classification Search ............... None
See application file for complete search history.

(56) References Cited

U.S. PATENT DOCUMENTS

| | | | | |
|---|---|---|---|---|
| 4,772,547 | A * | 9/1988 | Heimer et al. .............. 435/5 |
| 5,135,736 | A | 8/1992 | Anderson et al. |
| 5,831,016 | A * | 11/1998 | Wang et al. .............. 530/350 |
| 2002/0077288 | A1 | 6/2002 | Frangione et al. |

FOREIGN PATENT DOCUMENTS

| | | |
|---|---|---|
| EP | 0 497 997 A1 | 8/1992 |
| WO | WO90/11092 A1 | 10/1990 |
| WO | WO 90/11092 A1 * | 10/1990 |
| WO | WO96/10038 | 4/1996 |
| WO | WO96/12009 | 4/1996 |
| WO | WO00/35949 A1 | 6/2000 |

OTHER PUBLICATIONS

Buschle et al (PNAS USA 94: 3256-3261, Apr. 1997).*
Kim et al (J. Immunol. 159(4): 1666-1668, Aug. 1997).*
Celluzzi et al (J. Exp. Med. 1996, 183: 283-287).*
Bennett et al., *Nature*, 393:478-480 (1998).
Brossart et al., *J. Immunol.*, 158:3270-3276 (1997).
Bruschle et al., *PNAS*, 94:3256-3261 (1997).
Czerniecki et al., *J. Immunol.*, 159:3823-3837 (1997).
Greenberg et al., *Advances in Immunol.*, 49:281-355 (1991).
Guermonprez et al., *J. Immunol.*, 162(4):1910-1916 (Abstract) (1999).
Jameson et al., *J. Exp. Med.*, 177:1541-1550 (1993).
Kim et al., *J. Immunol.*, 159:1666-1668 (1997).
Layton et al., *Journal in Immunol.*, 151(2):1097-1107 (1993).
Newell et al., *PNAS*, 90:10459-10463 (1993).
Osicka et al., *Infect. Immunol.*, 68(1):247-256 (2000).
Ridge et al., *Nature*, 393:474-478 (1998).
Truman et al., *Exp. Hematol.*, 24:1409-1415 (1996).
Vidovic et al., *Eur. J. Immunol.*, 25:3349-3355 (1995).
Laus et al., "Enhanced major histocompatibility complex class I-dependent presentation of antigens modified with cationic and fusogenic peptides", *Nature Biotechnology*, 18:1269-1272 (2000).

* cited by examiner

*Primary Examiner*—G. R Ewoldt
*Assistant Examiner*—DiBrino Marianne
(74) *Attorney, Agent, or Firm*—Susan J. Meyers Fitch; Peter J. Dehlinger; King & Spalding LLP (57) ABSTRACT

Compositions and methods for eliciting an in vivo cytotoxic lymphocyte (CTL) response against a modified soluble protein antigen are disclosed. The modified soluble protein antigen comprises an added peptidic sequence which facilitates entry of the modified antigen into antigen presenting cells (APC).

5 Claims, 8 Drawing Sheets

COMPOSITIONS AND METHODS FOR ENHANCEMENT OF MAJOR HISTOCOMPATIBILITY COMPLEX CLASS I RESTRICTED ANTIGEN PRESENTATION

This application claims priority to U.S. Provisional Application Ser. No. 60/112,324, filed Dec. 14, 1998, now abandoned, and U.S. application Ser. No. 09/461,684, filed Dec. 14, 1999, now pending, both of which are expressly incorporated herein by reference.

FIELD OF THE INVENTION

The present invention relates to compositions of soluble protein antigens (Ag) which have been modified to render them presentable in the context of major histocompatibility complex class I molecules (MHC class I), methods for the use of such modified Ag compositions as effective vaccines for in vivo immunotherapy, and pharmaceutical compositions comprising the same.

The invention further relates to methods for treating antigen presenting cells (APC), wherein such treatment enhances the presentation of soluble protein antigens in the context of MHC class I.

REFERENCE TO SEQUENCE LISTING, TABLE OR COMPUTER PROGRAM

A "Sequence Listing" has been submitted with this application in the form of a text file, created 14 Aug. 2008, and named "57636-8020.US01SEQLIST.txt" (4,608 bytes), the contents of which are incorporated herein by reference in their entirety.

BACKGROUND OF THE INVENTION

Tumor specific $CD8^+$ cytotoxic T lymphocytes (CTL) appear to constitute an important effector limb of the antitumor immune response as indicated by animal model studies (Greenberg, 1991, *Adv. Immunol.* 49: 281). Therefore, tumor specific Ag recognized by CTL are likely to function as tumor rejection Ag, capable of inducing protective immunity in vivo.

MHC class I and class II molecules, constitutively expressed on APC, are responsible for the presentation of non-overlapping Ag-derived peptides to $CD8^+$ CTL and $CD4^+$ helper T cells (Th), respectively (Rothbard et al., 1987, *Nature* 326: 881; Babbitt et al., 1985, *Nature* 317: 359). CTL recognize class I molecules containing peptidic fragments of intracellular proteins that have been transported into endoplasmic reticulum prior to their transfer to the MHC molecule (Germain, 1995, *Ann. NY Acad. Sci.* 754:114; Heemels & Ploegh, 1995, *Annu. Rev. Biochem.* 64:463), while the bulk of class II complexed peptides presented to Th cells are degradation products of exogenous or cell surface proteins that enter the biosynthetic pathway of class II molecules via endocytosis and a subsequent fusion with lysosomes (Cresswell, 1994, *Annu. Rev. Immunol.* 12: 259). This dichotomy of Ag presentation explains why Ag-specific $CD8^+$ CTL are generated most effectively against intracellular Ag, or when the extracellular Ag are delivered into the cytosol. Since intact proteins in the extracellular medium do not ordinarily penetrate into the cytosol, soluble proteins typically fail to elicit CTL responses (Braciale et al., 1987, *Immunol. Rev.* 98: 95).

It is therefore desirable to provide a method for eliciting CTL responses against soluble proteins.

SUMMARY OF THE INVENTION

The present invention provides novel compositions and methods for eliciting an in vivo cytotoxic lymphocyte (CTL) response against a soluble protein antigen.

In one aspect, a modified soluble protein antigen capable of eliciting an enhanced CTL response is provided by the invention. The modification comprises the covalent addition of a peptidic sequence to the antigen which facilitates entry of the modified antigen into antigen presenting cells (APC).

In some cases, the added peptidic sequence is a peptide having about 20 to 25 amino acid residues which may or may not have an N-terminal cysteine residue.

The peptidic sequence may be chemically linked to the soluble protein antigen and to one or more other peptidic sequences or a conjugate of a soluble protein antigen and one or more of such peptidic sequences is formed by expression of a continuous nucleic acid coding sequence.

The invention also provides an antigenic composition for in vivo immunotherapy of a mammal, comprising one or more modified antigens, each having an added peptidic sequence.

In one aspect, the one or more modified protein antigens of the invention are specific to a given tumor or pathogen and may be used for treatment of a malignant tumor in a mammal.

In a further aspect, the invention provides an immunization method, e.g., for cancer therapy, wherein the method includes the steps of obtaining a sample of DC from a subject, exposing the DC to a modified soluble protein antigen in vitro in a manner effective to induce cell-surface presentation of one or more peptide antigens against which an immune response is desired, and returning the exposed and stimulated DC to the subject.

These and other objects and features of the invention will become more fully apparent when the following detailed description is read in conjunction with the accompanying drawings.

BRIEF DESCRIPTION OF THE DRAWINGS

FIGS. 2A, 2B and 2C each represent an independent experiment. In each case cpm represents cell growth measured by incorporation of [$^3$H]thymidine present during the final 6 h culture period. The "EL-4" and "E.G7-OVA" lines indicate the level of B3Z response to the negative and positive control APC, respectively, in the absence of additional soluble Ag.

DETAILED DESCRIPTION OF THE INVENTION

I. Definitions

Unless otherwise indicated, the terms below have the following meanings:

As used herein, "presentation of soluble protein antigens in the context of major histocompatibility complex class I molecules (MHC I)" means the soluble protein antigen or fragments thereof, are displayed together with major histocompatibility complex class I molecules on the cell surface and can serve as an inducer and target of class I restricted antigen-specific CTL.

As used herein, the term "pulse" means exposure of APC to antigen for a time sufficient to promote presentation of that antigen on the surface of the APC. APC which have been pulsed and present antigen on the APC surface are said to be "stimulated".

"Precursor antigen presenting cells" are cells that when exposed to an Ag or peptide are capable of becoming APC and presenting Ag to T cells.

As used herein, "antigen presenting cells" (APC) are any cells which, after being pulsed with Ag or peptide, can activate CD8$^+$ cytotoxic T-lymphocytes (CTL) or CD4$^+$ helper T-lymphocytes in an immune response.

"Dendritic cell precursors", or "DCP", are peripheral blood cells which can mature into DC under suitable conditions. DCP typically have a non-dendritic morphology and are not competent to elicit a primary immune response as antigen presenting cells.

"Dendritic cells", or "DC" are matured DCP, which typically have a dendritic cell morphology, that is, they are large veiled cells which extend dendrites when cultured in vitro. When pulsed with Ag or peptide, such DC are capable of presenting Ag to naïve T cells.

As used herein, the term "modified antigen presenting cells" (modified APC) refers to a population of APC which have been treated ex vivo such that they have an enhanced ability to present antigen in the context of MHC class I relative to APC which have not been modified.

Similarly, as used herein, the term "modified dendritic cells" (modified DC) refers to a population of DC which have been treated ex vivo such that they have an enhanced ability to present antigen in the context of MHC class I relative to DC which have not been modified.

The term "more effectively" when used herein relative to the presentation of soluble proteins antigens means at least a 5-fold increase in the magnitude of detectable T cell response following presentation of a soluble protein antigen by APC. For example, in one case this means at least a 5 fold increase in the number of responder cells is detected following presentation of a given antigen by a designated number of APC relative to the number of detectable responder cells obtained when the same number of APC from a reference population present the same antigen under the same culture conditions. In another case, this means that at least a 5-fold increase in the magnitude of T cell response is detected following presentation of a given antigen by a designated number of APC relative to magnitude of T cell response obtained when a different or modified antigen is presented by the same number of APC under the same culture conditions and at an equimolar Ag concentration.

As used herein, the terms "tumor" and "cancer" are used interchangeably and refer to a cell that exhibits a loss of growth control and forms unusually large clones of cells. Tumor or cancer cells generally have lost contact inhibition and may be invasive and/or have the ability to metastasize.

II. Immune Response to Soluble Protein Antigens

In experimental systems, tumor antigen specific cytotoxic T lymphocytes (CTL) are the most powerful immunological mechanism for the elimination of tumors. CTL can be induced either in vivo with vaccines or can be generated in vitro and then be re-infused into the tumor-bearing organism. The in vivo induction of CTL is typically accomplished by immunization with live virus or cells (Tanaka, et al., *J. Immunol.*, (1991), 147, 3646-52, Wang, et al., *J. Immunol.*, (1995), 4685-4692).

Except for a few special viral proteins such as the SV40 large T antigen and the Hepatitis B surface antigen, injection of isolated or soluble proteins does not result in induction of CTL (Schirmbeck, et al., *Eur. J. Immunol.*, (1993), 23, 1528-34). CTL are induced when a protein enters the major histocompatibility complex class I ("MHC I" or "class I") pathway of antigen processing. To enter this pathway the protein must be present in the cytosol of an antigen presenting cell (APC). There it is degraded into peptides which are then transported into the endoplasmic reticulum, where they associate with HLA class I molecules. These peptides are then displayed together with the class I molecules on the cell surface and can serve as an inducer and target of class I restricted antigen-specific CTL. Physiologically, only proteins that are endogenously synthesized by the APC enter this pathway.

The priming of an immune response expands and activates "naive" lymphocytes, i.e., those that have not previously seen an immunogen to become "effector" cells that actively respond. Each naive cell has the potential for seeing one and only one antigenic epitope, a situation analogous to a key fitting into a lock. Only those cells that recognize their cognate epitope become effector cells.

T-cells can be of the "helper" or "cytotoxic" (cytotoxic) type. Helper T cells secrete growth factors for lymphoid cells that stimulate the activation and function of B and T cells. The cytotoxic T cells recognize and either directly, or indirectly, kill cells that express a particular antigen. Like B cells, each T cell has receptors specific for one and only one antigenic epitope. T cell receptors recognize fragments of proteins that are displayed on the cell surface by major histocompatibility complexes (MHC).

There are two different types of MHC proteins, Class I and Class II, both of which present proteolytically degraded fragments of proteins to T cells. Class I molecules which are expressed on most cells of the body and present fragments of endogenously synthesized proteins to cytotoxic T cells. Class II molecules which are expressed on specialized antigen presenting cells (APCs) such as macrophages, monocytes, dendritic cells and B cells present protein fragments to T helper cells. (Chen, C H and Wu, T C, *J Biomed Sci.*, 5(4):231-52 1998)

In most cases, Class I molecules present foreign proteins synthesized in a cell. For presentation by Class II, the foreign protein either can be synthesized in the cell or taken up by the cell from the outside (i.e., presented in the form of a free protein or peptide). If an antigen is synthesized in a cell and presented by both Class I and Class II molecules, both antibody producing B cells and cytotoxic T cells are produced. However, if an antigen originated outside of a cell and is expressed only by Class II, the specific immune response is largely limited to T helper cells and antibody production. [THE SCIENTIFIC FUTURE OF DNA FOR IMMUNIZATION, American Academy of Microbiology, Robinson, et al., Eds., 1-29, 1997]

Accordingly, the typical response to soluble protein antigens is a Class II mediated response. The present invention represents compositions and methods which allow soluble protein antigens to enter the Class I pathway which is typically reserved for foreign cellular antigens.

In addition, some progeny of antigen-stimulated T cells do not develop into effector cells, but become memory cells that are capable of surviving for long periods of time in the absence of additional antigenic challenge. Such memory cells are quiescent and do not produce effector molecules unless they are stimulated by antigen. (See, e.g., Abbas, A K et al., Eds. CELLULAR AND MOLECULAR IMMUNOLOGY, W. B. Saunders Co., pages 116-123; 130-134, 1997)

Naïve T cells (or T cells that have not been previously exposed to a given antigen) require only the correct MHC I-restricting molecule to survive, however to expand, they also must be exposed to antigen. In contrast, memory T cells have a lower functional activation threshold that facilitates secondary responses which are more rapid and stronger than that of naïve T cells.

III. Modified Soluble Protein Antigen Compositions

The present invention is based on the discovery that when peptidic sequences such as those presented as pK (SEQ ID NO:1) and pEA (SEQ ID NO:2), are covalently linked to an antigen, the antigen is capable of triggering naive CTL responses in vivo, and is about 100 fold more efficient in stimulating corresponding class I restricted memory T cells in vitro.

The added peptidic sequence generally comprises a peptide having about 20 to 25 amino acid residues. In one preferred embodiment, the peptidic sequence comprises a combination of lys and arg residues (SEQ ID NO:7). In some cases this sequence has an added N-terminal cysteine residue (SEQ ID NO:6) for purposes of chemical coupling.

In another preferred embodiment, the peptidic sequence comprises repeating subunits having about 6 amino acids per subunit wherein a given sequences has 3 or more of such subunits and may or may not have an added N-terminal cysteine. Exemplary peptides are presented as CYS-[X-Y-Y-Y-Y-Y]$_n$ (SEQ ID NO: 8); wherein X=glu or asp, Y=ala, leu, ile, phe, gly, cys, met or val and n is greater than or equal to 3, with a specific example provided by the pEA peptide presented as SEQ ID NO:2.

The modified soluble protein antigen may be chemically linked to one or more peptidic sequences or may be formed by expression of a continuous nucleic acid coding sequence comprising one or more of said peptidic sequences, as exemplified by SEQ ID NO:4 and SEQ ID NO:5.

When such peptidic sequences are chemically linked to one or more other peptidic sequences, the sequences may or may not have an N-terminal cysteine.

In another preferred embodiment, the present invention provides an antigen composition for in vivo administration comprising one or more soluble protein antigens covalently conjugated to peptides selected from the group consisting of the pK, pEA, HA, tandem pEA/pK, tandem HA/pK peptides, peptides comprising lysine and arginine residues and peptides comprising repeating subunits presented as SEQ ID NO:1, SEQ ID NO:2, SEQ ID NO:3, SEQ ID NO:4, SEQ ID NO:5, SEQ ID NO:6, SEQ ID NO:7, the sequences designated sequence number 8 and sequence number 9, respectively (Table 1).

In a further preferred embodiment, the one or more soluble protein antigens is covalently conjugated to the pK peptide (SEQ ID NO: 1) and the pEA peptide (SEQ ID NO: 2), such that the conjugate enters the class I MHC presentation pathway, consequently stimulating antigen specific $CD8^+$ CTL.

Modified soluble protein antigens having added peptidic sequences can also be formed recombinantly as fusion proteins according to methods known in the art, as further described below.

Although the exemplified compositions with enhanced antigen presentation activity comprise peptides with sequences presented as SEQ ID NO: 6, SEQ ID NO: 7 and the sequences designated as sequence number 8 and sequence number 9 in Table 1, below covalently conjugated to an antigen, as detailed in Example 1, it will be understood that other peptides may be used to obtain the same effect on naive CTL responses in vivo, and class I restricted memory T cells in vitro.

An exemplary application of the antigenic compositions of the present invention is the use of pEA/pK-conjugated form of an antigen which is expressed by and isolated from tumor cells, in an antigenic composition for administration to a cancer patient (i.e., a "vaccine"). Such an antigenic composition can provide effective immunotherapy for various tumors, such as, but not limited to prostate and breast carcinoma, multiple myeloma, etc.

As shown in Example 2, this treatment is particularly effective when the pK (SEQ ID NO: 1) and the pEA peptides (SEQ ID NO: 2) are conjugated to an antigen expressed by and isolated from tumor cells which is co-cultured with DC to activate them ex vivo, followed by administration to a subject.

IV. Production of Recombinant Fusion Proteins

Modified soluble protein antigens having one or more added peptidic sequences may also be produced recombinantly as fusion proteins by expression of continuous nucleic acid coding sequences according to methods known in the art.

Unless otherwise indicated, all terms used herein have the same meaning as they would to one skilled in the art of the present invention. Practitioners are particularly directed to Sambrook et al. (1989) MOLECULAR CLONING: A LABORATORY MANUAL (Second Edition), Cold Spring Harbor Press, Plainview, N.Y. and Ausubel F M et al. (1989) CURRENT PROTOCOLS IN MOLECULAR BIOLOGY, John Wiley & Sons, New York, N.Y., for definitions and techniques routinely used by those of skill in the art.

The invention includes modified soluble antigen fusion proteins produced using recombinant techniques. Such fusion proteins are produced by culturing recombinant prokaryotic or eukaryotic host cells comprising nucleic acid sequences encoding the fusion protein under conditions promoting expression of the fusion proteins, followed by recovery of the modified soluble antigen fusion proteins from the host cells or the cell culture medium.

The nucleic acid coding sequence for the fusion protein may be inserted into any one of a variety of expression vectors for expressing a polypeptide, as long as it is replicable and viable in the host. In general, DNA is inserted into an appropriate restriction endonuclease site(s) using routine techniques. Such procedures and related sub-cloning procedures are deemed to be within the scope of those skilled in the art. The vector may comprise regulatory sequences, including, for example, non-coding sequences, such as introns and control elements, i.e., promoter and terminator elements or 5' and/or 3' untranslated regions, effective for expression of the coding sequence in a suitable host and/or in a vector or host environment in which the modified soluble protein antigen coding sequence is not normally expressed, operably linked to the coding sequence. Large numbers of suitable vectors and promoters are known to those of skill in the art, are commercially available and are described in Sambrook, et al., (supra).

The present invention also relates to host cells which are genetically engineered with vectors useful to produce the modified soluble antigen fusion proteins of the invention by recombinant techniques. Host cells are genetically engineered (i.e., transduced, transformed or transfected) with an appropriate vector which may be, for example, a cloning or expression vector. The vector may take the form of a plasmid, a viral particle, a phage, etc. The culture conditions, such as temperature, pH and the like, are those previously used with the host cell selected for expression, and will be apparent to those skilled in the art.

Methods of introducing nucleic acids into cells for expression of heterologous proteins are also known to the ordinarily skilled artisan, for example, calcium phosphate transfection, DEAE-Dextran mediated transfection, electroporation, nuclear microinjection, bacterial protoplast fusion with intact cells, or use of polycations, e.g., polybrene, polyornithine, may be used. General aspects of transformation involving mammalian cells have been described in U.S. Pat. No. 4,399, 216, and Keown et al., *Methods in Enzymology*, 185:527-537 (1990), both or which are expressly incorporated by reference herein.

Suitable host cells for cloning or expressing the DNA in the vectors herein include prokaryote, yeast, or higher eukaryotic cells. Suitable prokaryotes include but are not limited to eubacteria, such as gram-negative or gram-positive organisms, for example, *E. coli*.

Suitable host cells for the expression of glycosylated soluble antigen fusion proteins are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. The selection of the appropriate host cell is deemed to be within the skill in the art.

A process for producing such soluble antigen fusion proteins comprises culturing host cells under conditions suitable for expression of the fusion protein and recovering the fusion protein from the cell culture. In general, principles, protocols, and practical techniques for maximizing the productivity of cell cultures can be found in MAMMALIAN CELL BIOTECHNOLOGY: A PRACTICAL APPROACH, M. Butler, ed. (IRL Press, 1991) and Sambrook et al., supra. More specifically, techniques for expression in the Baculovirus system are described in Engelhard E K et al. *Proc. Nat. Acad. Sci.* 91:3224-3227, 1994, expressly incorporated by reference herein.

Host cells transformed with nucleotide sequences encoding the soluble antigen fusion proteins of the invention may be cultured under conditions suitable for the expression and recovery of the encoded protein from cell culture. The protein produced by a recombinant cell may be secreted, membrane-bound, or contained intracellularly depending on the sequence and/or the vector used.

As understood by those of skill in the art, expression vectors containing polynucleotides encoding the modified soluble protein antigens of the invention can be designed with signal sequences which direct secretion of such modified antigens through a prokaryotic or eukaryotic cell membrane.

The modified soluble proteins antigens of the invention whether produced by chemical coupling or by expression of continuous coding sequences as recombinant fusion proteins may be used to pulse APC, and be presented by such APC in the context of MHC I.

V. Antigen Presenting Cells

A. Enrichment of DC

Although exemplified methods include cell adherence to tissue culture plastic, which achieves the enrichment of DC, it will be understood that other approaches may be used to obtain such a cell fraction. For example, combined density gradient centrifugation and affinity cell separation may be used.

DC have been isolated and purified using a variety of methodologies incorporating, for example, multiple-step density-gradient based isolation, monoclonal antibody panning, depletion of lineage positive cells and serum-supplemented cultures (Macatonia, S. E., et al., *Immunology* 74:399-406, 1991; Markowicz, S., and Engleman, E. G., *J. Clin. Invest.* 85:955-961, 1990; Young, J. W., and Steinman, R. M., *Cell. Immunol.* 111:167-182, 1987).

In one exemplary method, DC are obtained from peripheral blood by performing the steps of (1) standard leukapheresis; (2) buoyant density centrifugation either with a one-step or successive two-step procedure; and (3) culture of the cells ex vivo in serum free medium for 40 hours, in the absence of exogenously added cytokines. If desired, DC can be further enriched by (4) post-culture enrichment by buoyant density centrifugation; and (5) depletion of monocytes/macrophages and B lymphocytes using CD14 and CD19 immunomagnetic beads. (See, e.g., co-owned, copending U.S. Ser. No. 60/087, 764, expressly incorporated by reference herein.)

The DC so isolated are characterized by their dendritic morphology and by a phenotype that is positive for surface expression of HLA-DR (human leukocyte antigen, DR) and negative for surface antigens specific to particular cell lineages (i.e., CD3, CD14, CD16, CD19, CD20 and CD56 negative; designated herein as, "lin −"), and the ability to elicit primary and secondary immune responses when co-cultured with human lymphocytes. (See, e.g., co-owned, copending U.S. Ser. No. 60/158,618, expressly incorporated by reference herein.)

B. Evaluation of Antigen Presentation

An antigen presentation assay is used to evaluate the antigen presenting ability of APC (or DC) and to evaluate the presentation of various antigens. An exemplary assay is described in Example 1, wherein APC (exemplified by EL4 cells), are pulsed with antigen, followed by antigen presentation by the APC to responder cells (exemplified by B3Z cells), with an evaluation of responder proliferation by $^3$H incorporation. The assay format described herein may be used to evaluate the antigen presenting ability of APC by using a fixed amount of antigen in the pulsing step together with a titration of APC or the addition of a fixed number of APC subjected to various treatments to activate them. Alternatively, the assay format may be used to evaluate the ability of various antigen to be presented by using a titration of the antigen together with a fixed number of APC. In each case, the endpoint is a measurement of the corresponding proliferation of responder cells as indicated by ³H incorporation.

As described in Example 1, when EL-4 APC were pulsed with a conjugate comprising the pK peptide (SEQ ID NO: 1) and the pEA peptide (SEQ ID NO: 2), or the pK peptide (SEQ ID NO: 1) and the HA peptide (SEQ ID NO: 3) linked to the OVA antigen at a concentration equivalent to the nonstimulatory (i.e., suboptimal) dose of native OVA, both conjugates triggered positive responses. Among the two, the OVA-pK/pEA conjugate was more potent.

Figure 2A:
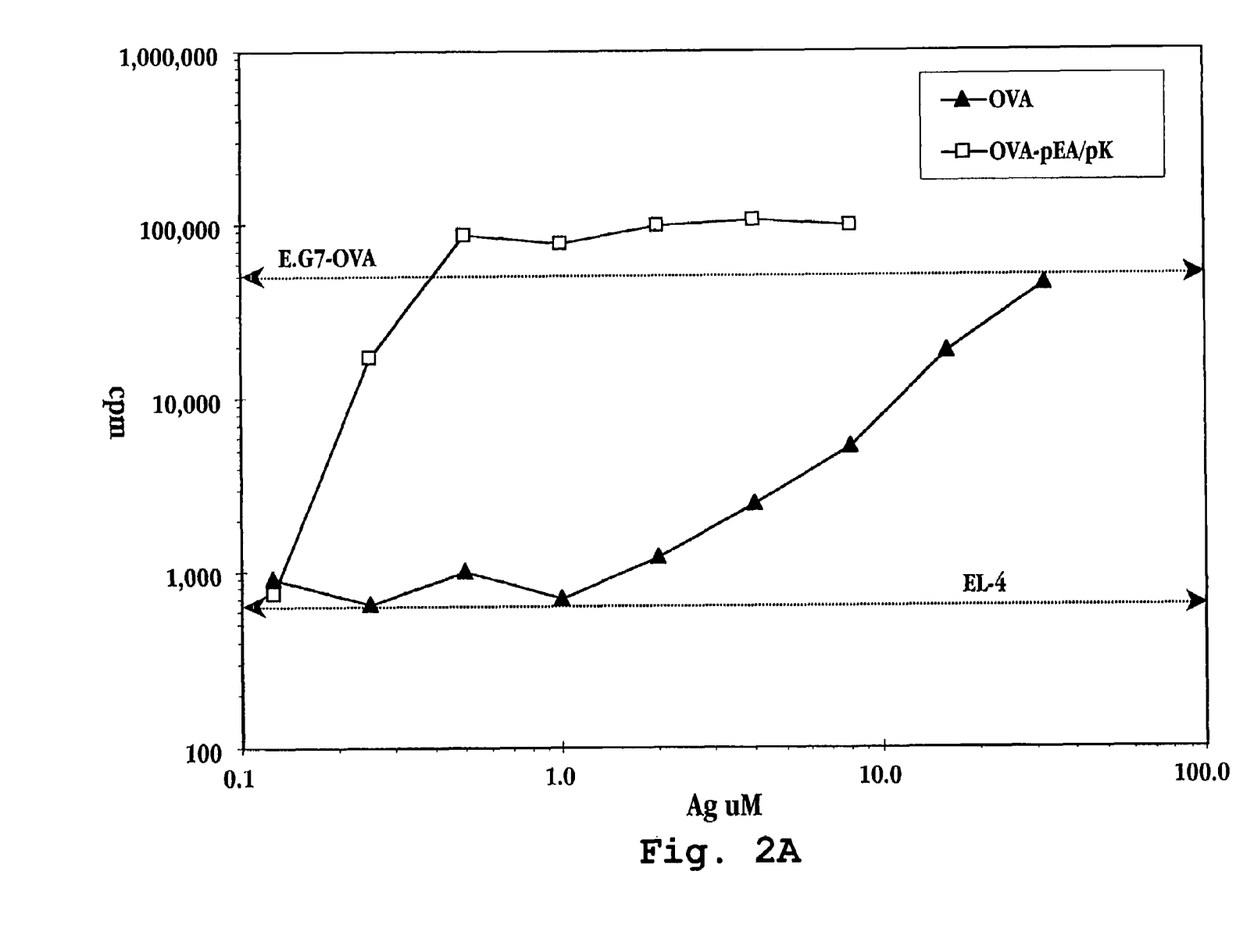
FIGS. 2A-C show the response of the B3Z T cell hybridoma to EL4 APC pre-pulsed with OVA or OVA-pEA/pK preparations at different Ag concentrations.
Figure 2B:
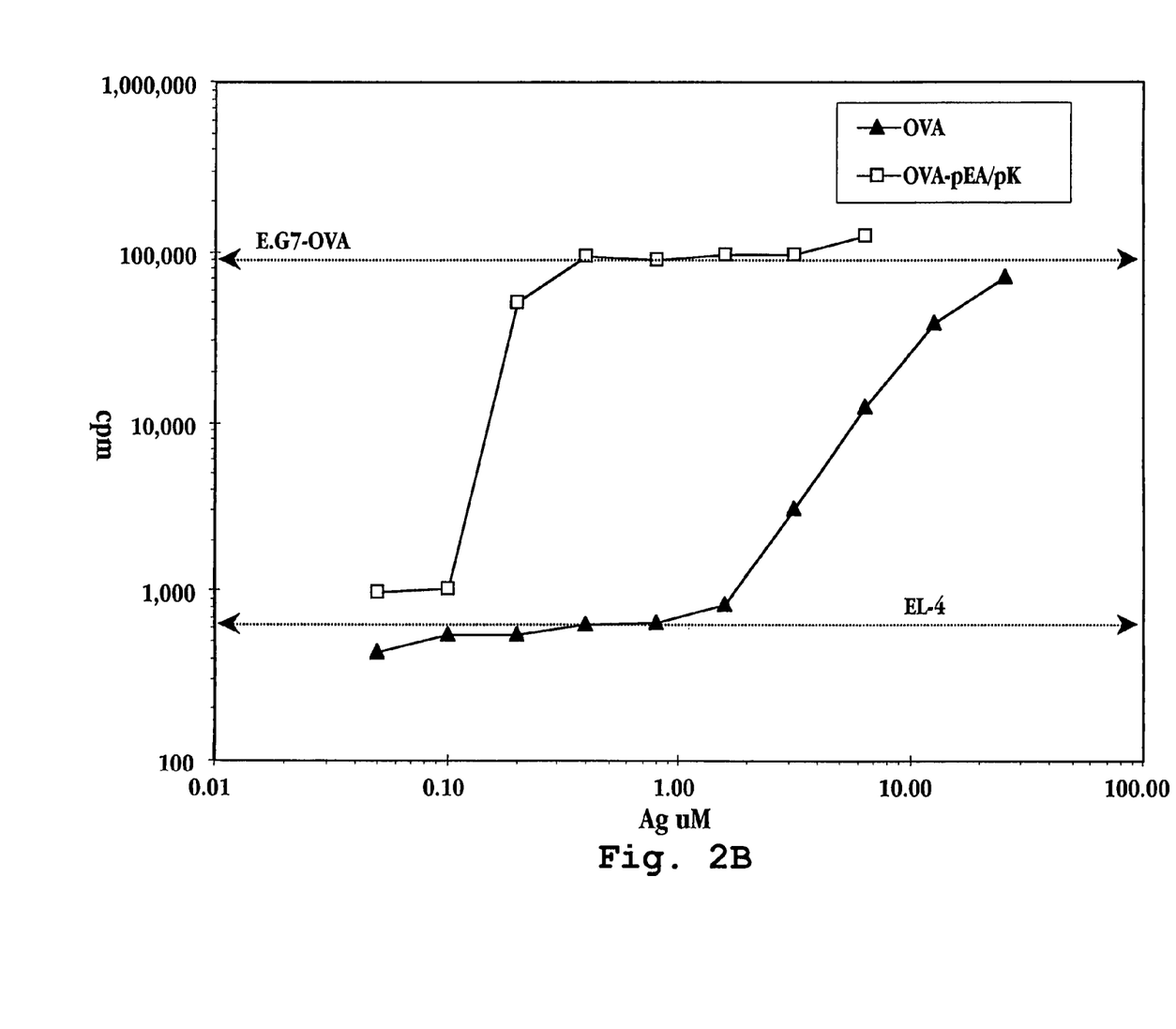
Figure 2C:
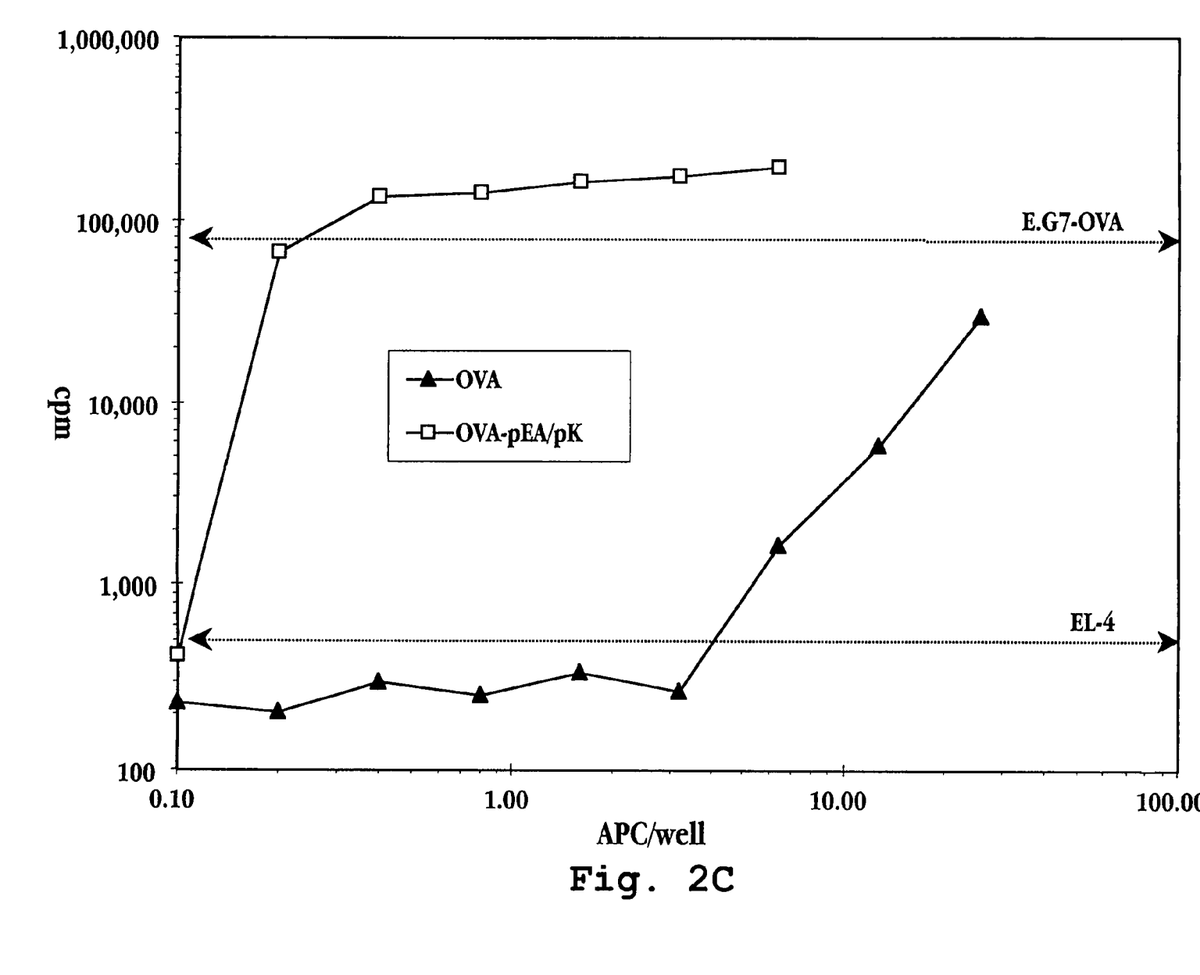
Figure 3:
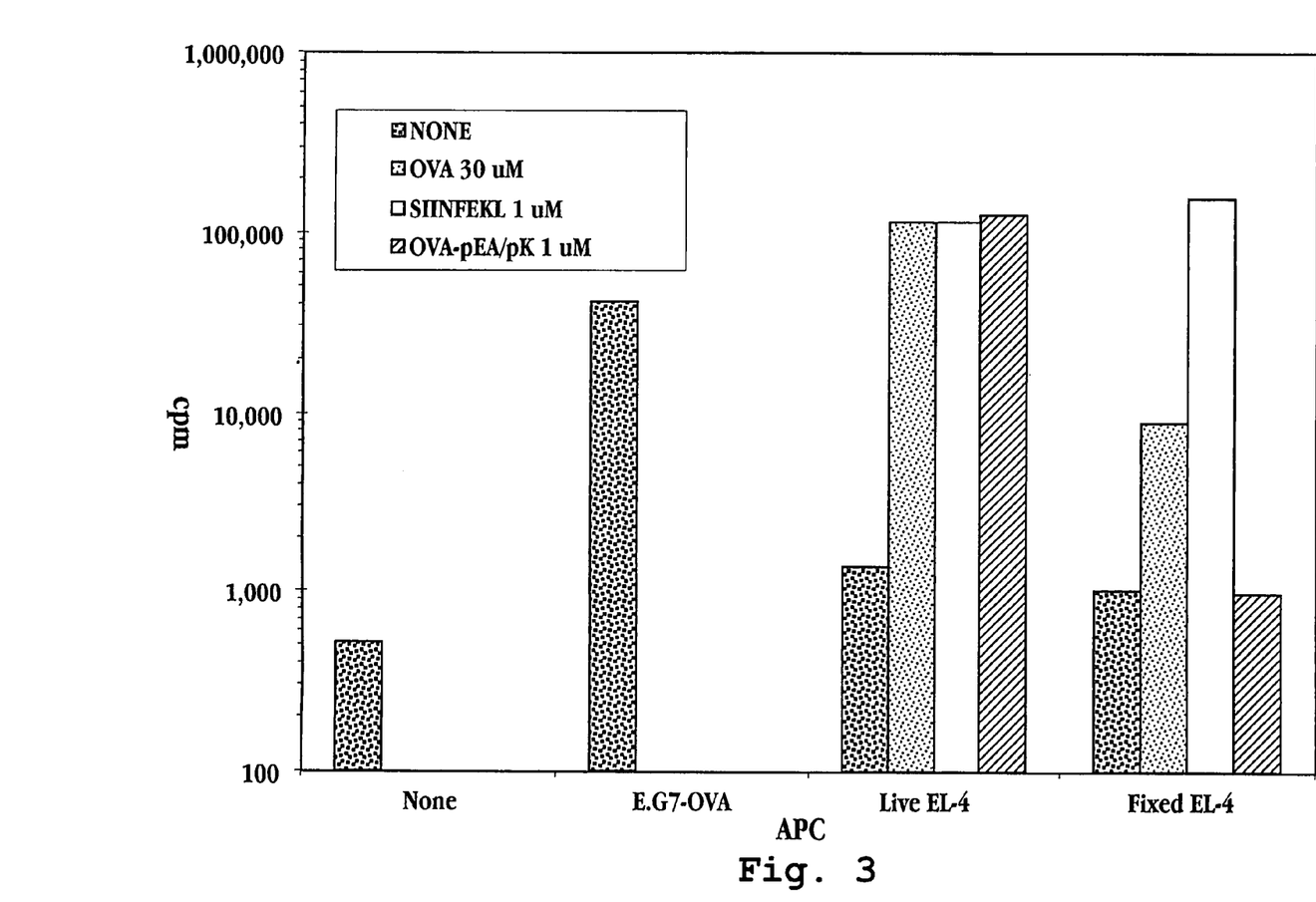
FIG. 3 shows the response of B3Z T cell hybridomas to APC pre-pulsed with SIINFEKL, or OVA or OVA-pEA/pK at their respective optimal concentrations. Cpm corresponds to cell growth as described above for FIGS. 2A-C.

When EL-4 APC were pre-pulsed with a wide range of antigen concentrations, it was observed that the pEA/pK-conjugate of OVA is about 100 fold more efficient in stimulating antigen presentation than unconjugated OVA. (See FIGS. 2A-C)

A characteristic of DC, a potent subset of APC, is their ability to trigger in vivo responses of naïve CD8⁺ cytotoxic T-lymphocytes (CTL), after being pulsed with antigen (Ridge et al. 1998 *Nature* 393:474). As exemplified herein, DC are able to induce a CTL response in mammals not previously exposed to a soluble protein antigen when the antigen was modified by conjugation with pEA/pK, but not when an unmodified form of the antigen was used to pulse the DC.

Figure 5A:
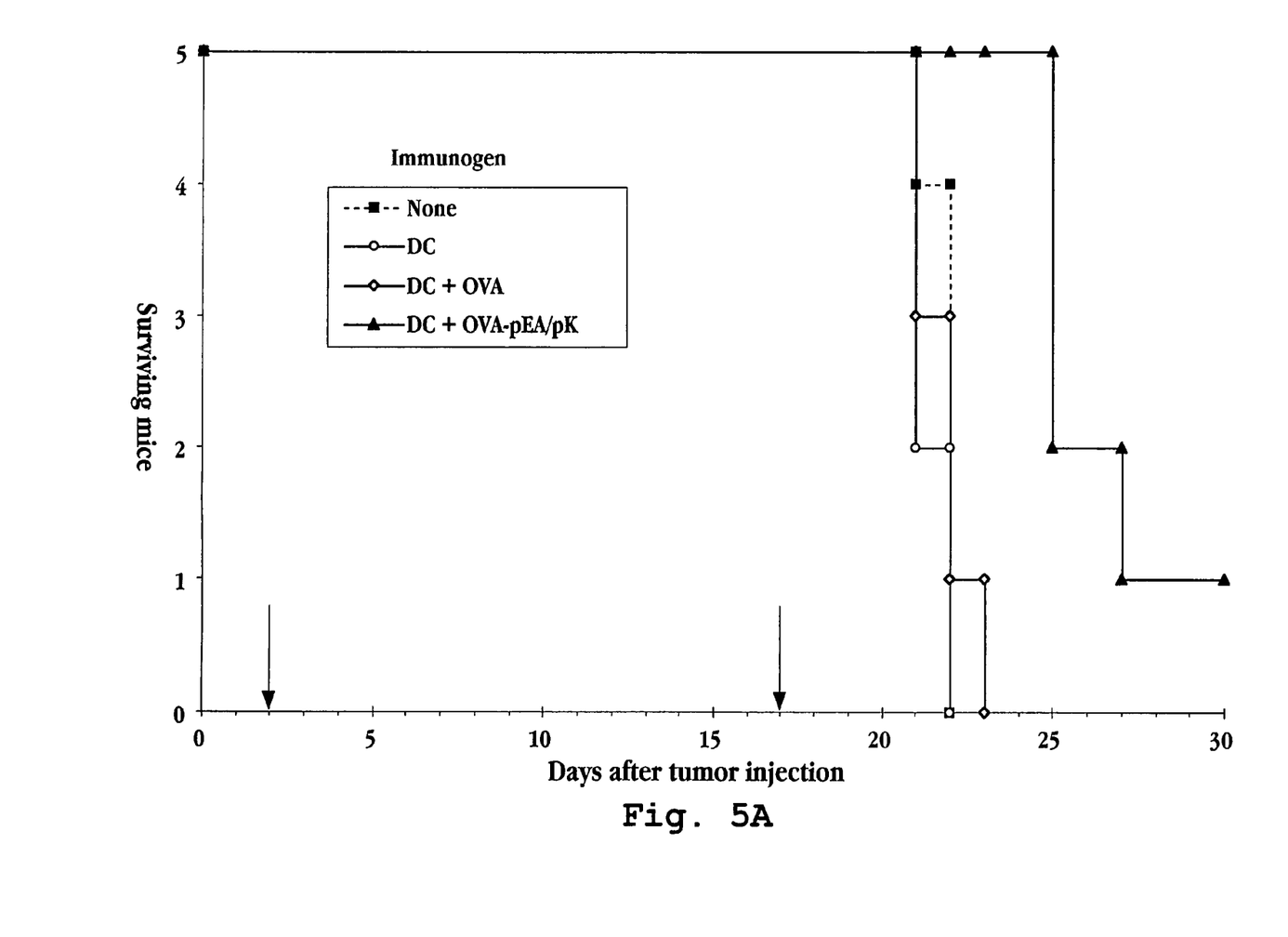
FIGS. 5A-B show the survival of E.G7-OVA injected mice treated with Ag-pulsed APC. Twenty 8-week old randomized female C57BL/6 mice were injected i.p. with $25\times10^6$ and $2\times10^6$ E.G7-OVA cells in 0.1 ml PBS (FIG. 6A and FIG. 6B, respectively). Two days and again 2 weeks later (arrows), mice received i.p. injections of DC, OVA-pulsed DC, OVA-pEA/pK-pulsed DC ($5\times10^5$ cells per 0.1 ml injection), or PBS. Mice were monitored daily and their survival was recorded as indicated.
Figure 5B:
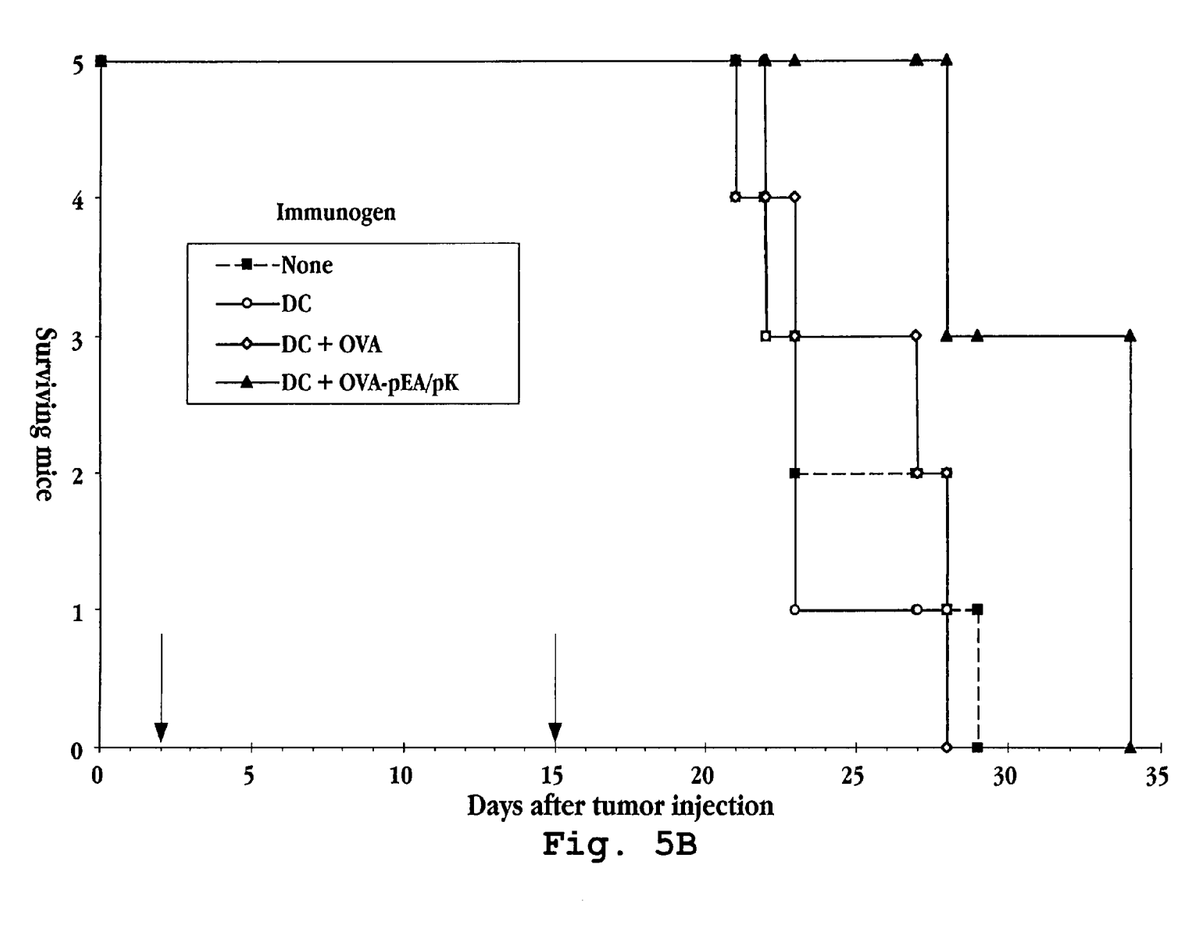

The superior immunogenicity of the OVA antigen modified by conjugation to the pK peptide (SEQ ID NO: 1) and the pEA peptide (SEQ ID NO: 2), as determined by stimulation of a CD8⁺-mediated immune response is further detailed in Example 2. The Example describes the increased survival of mice bearing OVA-expressing tumor cells when injected with DC pre-pulsed with pEA/pK-conjugated OVA prior to injection relative to the response to DC pre-pulsed with OVA alone. (see FIG. 6A-B).

It will be understood that any of a number of methods may be used to pulse APC with antigen, to make them effective to present antigen in the context of MHC I. The experiments detailed herein demonstrate that activation of DC by exposure to modified antigenic peptides facilitates processing of the peptides through the "endogenous" class I pathway such that they are presented in association with MHC class I molecules, and accordingly are able to activate CD8⁺ CTL.

VI. Compositions and Methods for Immunotherapy and Cancer Therapy

One of the useful features of the antigenic compositions of the present invention is that they are able to more effectively present antigen for the induction of both CD8⁺ CTL-mediated as well as CD4⁺ Th cell proliferative responses than APC which have not been so modified.

As such, the antigenic compositions of the present invention are universally useful and can be employed in a wide range of immunotherapeutic, immunoprophylactic and cancer therapeutic applications involving generation of primary and secondary immune responses.

The invention also provides modified soluble protein antigens presented in the context of MHC Class I.

In a preferred embodiment, immunization with the modified soluble protein antigens of the invention results in an MHC Class I-mediated cellular immune response to a soluble protein antigen which would not elicit a cellular immune response if provided in an unmodified form. In a further preferred embodiment, immunization with such a modified soluble protein antigen results in an MHC Class I-mediated cellular immune response which is greater in magnitude and accordingly provides greater protection than a cellular immune response to the same antigen if provided in an unmodified form.

In a preferred embodiment, the present invention provides an antigenic composition comprising modified antigens and APCs, as described above, which is able to more effectively induce T-cell responses, than an antigenic composition comprising antigens which have not been so modified.

An antigenic composition comprising the combination of modified antigens and APCs yields a novel antigenic composition which finds utility in immunotherapy of a mammal and may function as a vaccine.

In a related aspect, the invention includes a method of immunizing a subject against an antigen, e.g., a known cancer or pathogen-specific antigen or immunogen. The method includes pulsing APC or DC with a selected antigen or immunogen wherein the antigen or immunogen has an added peptidic sequence (which facilitates entry of the antigen or immunogen into APC or DC), by exposing the APC or DC to the modified antigen in a manner effective to induce cell-surface presentation of one or more peptide antigens specific to the antigen or immunogen and returning the pulsed APC or DC to the subject.

The exposing step can be achieved either in vitro (ex vivo) or in vivo. For example, the modified antigen may be directly injected into a subject or the APC or DC of the subject exposed to the modified antigen in vitro (ex vivo), with the stimulated APC or DC returned to the subject.

In a further preferred embodiment the modified soluble protein antigen in the antigenic composition is a cancer-specific antigen or tumor antigen. Exemplary cancer-specific or tumor antigens known to those of skill in the art include, but are not limited to, PAP, HER2, MART-1, MAGE, BAGE, and GAGE.

In a related aspect, the cancer-specific or tumor antigen is modified by covalent conjugation to a peptide selected from the group consisting of the pK, pEA, HA, tandem pEA/pK, tandem HA/pK peptides, peptides comprising lysine and arginine residues and peptides comprising repeating subunits presented as SEQ ID NO:1, SEQ ID NO:2, SEQ ID NO:3, SEQ ID NO:4, SEQ ID NO:5, SEQ ID NO:6, SEQ ID NO:7 and the sequences designated as sequence number 8 and sequence number 9, respectively.

In a preferred embodiment, the cancer-specific or tumor antigen is modified by covalent conjugation to the pK peptide (SEQ ID NO: 1) and the pEA peptide (SEQ ID NO: 2).

Such antigenic composition comprising modified antigens alone or in combination with modified APC can be used, for example, in direct in vivo administration, ex vivo somatic therapy, in vivo implantable devices and ex vivo extracorporeal devices.

A related aspect of the invention comprises a method of immunizing a subject against a tumor or pathogen having a known tumor- or pathogen-specific antigen which includes the steps of; obtaining a population of APC or DC from a blood sample taken from a patient (subject), exposing the APC or DC to a modified tumor- or pathogen-specific antigen in vitro in a manner effective to induce cell-surface presentation of one or more peptide antigens against which an immune response is desired; and returning the pulsed APC or DC to the subject.

From the foregoing, it will be appreciated that the invention provides compositions and methods having the unique feature that processing of soluble protein antigens occurs through the MHC class I, as opposed to class II, pathway.

Although the invention has been described with reference to specific methods and embodiments, it is appreciated that various modifications and changes may be made without departing from the invention.

EXAMPLE 1

Evaluation of in vitro Presentation of OVA-peptide Conjugates

The IL-2 secreting mouse T cell hybridoma B3Z, which responds to the mouse MHC class I (H2-K$^b$) bound OVA-derived peptide SIINFEKL (OVA$_{257-284}$; Jameson et al., *J. Exp. Med.* 177: 1541, 1993; hereinafter SEQ ID NO: 10), was used to evaluate the presentation efficacy of various OVA-peptide conjugates by the thymoma cell line EL-4.

Grade VI (99% pure) chicken ovalbumin (OVA) purchased from Sigma (St. Louis, Mo.), was used either in its native or conjugated form. Peptide conjugates OVA-pEA, OVA-pK, OVA-HA, OVA-HA/pK and OVA-pEA/pK were prepared as custom reagents by a commercial manufacturer (Biosynthesis, Inc, Lewisville, Tex.) according to standard methods. E.G7-OVA is the EL-4 cell line transfected with full length OVA cDNA (Brossart et al., *J. Immunol.* 158: 3270, 1997).

Briefly, peptides Cys-Lys-Lys-Lys-Lys-Lys-Lys-Lys-Lys-Lys-Lys-Lys-Lys-Lys-Lys-Lys-Lys-Lys-Lys ("pK", SEQ ID NO: 1), Cys-Glu-Ala-Ala-Ala-Ala-Ala-Glu-Ala-Ala-Ala-Ala-Ala-Glu-Ala-Ala-Ala-Ala-Ala-Glu-Ala-Ala-Ala-Ala-Ala-Ala ("pEA", SEQ ID NO: 2) and Cys-Gly-Leu-Phe-Gly-Ala-lle-Ala-Gly-Phe-lle-Glu-Asn-Gly-Trp-Glu-Gly-Met-lle-Asp-Gly-Trp-Tyr-Gly ("HA", SEQ ID NO: 3) were synthesized by Fmoc chemistry on SPAR 50 polyamide resins. Peptides were purified by HPLC and conjugated to OVA with sulfo-MBS (m-maleimidobenzoyl-N-hydroxysulphosuccinimide ester).

Figure 1:
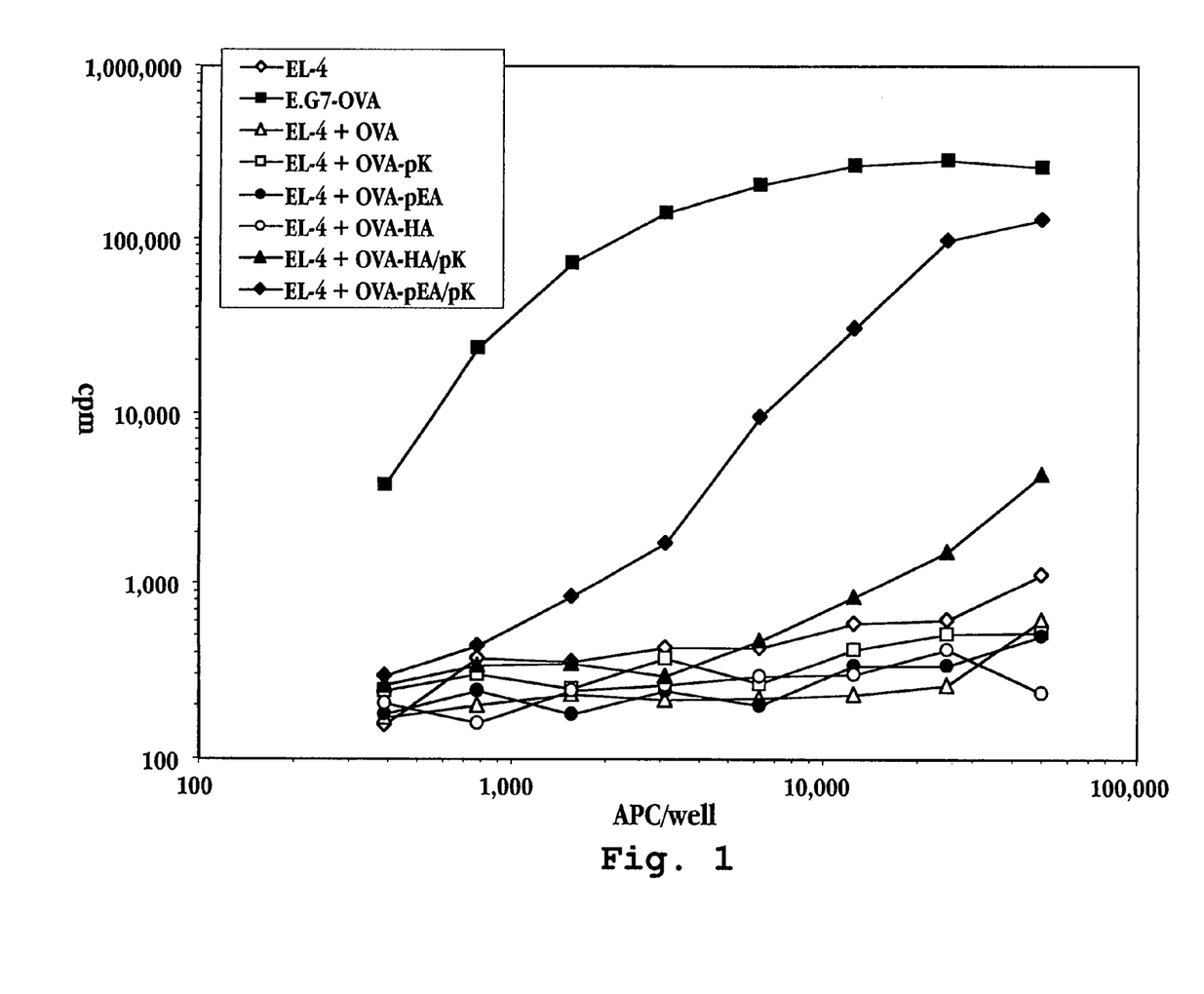
FIG. 1 shows the responses of interleukin-2 (IL-2) secreting mouse T cell hybridoma B3Z (Jameson et al., 1993, *J. Exp. Med.* 177: 1541) to various forms of ovalbumin (OVA) presented by the syngeneic APC line, EL-4. Cpm refers to counts per minute; HA refers to influenza virus hemagglutinin derived peptide, OVA refers to native ovalbumin; OVA-HA refers to the HA-conjugated form of OVA; OVA-PEA refers to the pEA-conjugated form of OVA; OVA-pK refers to the pK-conjugated form of OVA; OVA-HA/pK, refers to the HA and pK-conjugated form of OVA; and OVA-pEA/pK refers to the pEA and pK-conjugated form of OVA. E.G7-OVA is the EL4 cell line transfected with full length OVA cDNA (Brossart et al., *J. Immunol.* 158: 3270, 1997).

For the experiment shown in FIG. 1, cell cultures were maintained in DMEM medium supplemented with 10% FCS, 292 µg/ml of L-glutamine, 100 U/ml of penicillin, 100 U/ml of streptomycin and 55 µM of 2-ME (Gibco, Grand Island, N.Y.) at 37° C. in a humidified atmosphere containing 10% CO2. Mouse thymoma cells EL-4 were pulsed overnight at 37° C. with indicated antigens by co-culturing 1×10$^6$ cells with 2 µM of each antigen. Subsequently, pulsed APC were washed and gamma-irradiated (30 Gy), and an IL-2 secretion assay was performed as described previously (Kruisbeek, 1998, in Coligan et al. (eds.) *Current Protocols in Immunology*, Wiley, New York, N.Y., 1:3.14). Namely, 1×10$^5$ B3Z hybridoma cells were cultured in 0.2 ml microwells in the presence of a given number of APC (as shown in FIG. 1). One day later, culture supernatants were harvested and tested for their ability to support the proliferation of 10$^4$ HT-2 cells (an IL-2 dependent cell line) for 24 h. Cell growth was measured by [$^3$H]thymidine incorporation during the final 6 h culture period.

When EL4 cells were pulsed with antigen at a concentration equivalent to the nonstimulatory (i.e., suboptimal) dose of native OVA, neither OVA, OVA-pEA, OVA-HA nor OVA-pK stimulated B3Z above the background level, OVA conjugated to the pK peptide (SEQ ID NO: 1) and the pEA peptide (SEQ ID NO: 2) and OVA conjugated to the pK peptide and the HA peptide (SEQ ID NO: 3) triggered positive responses. Among the two, the OVA-pK/pEA conjugate was more potent. See Table 1, below, for exemplary peptidic sequences for addition to soluble protein antigens in the methods and compositions of the invention.

Tissue cultures for the experiments shown in FIGS. 2-5 were maintained in IMDM medium supplemented with 10% FCS, 2 mM L-glutamine, 0.1 mg/ml kanamycin sulfate and 3×10$^{-5}$ M 2-ME (Gibco, Grand Island, N.Y.) at 37° C. in a humidified atmosphere containing 5% CO$_2$ (tissue culture incubator). 10$^5$ hybridoma cells were cultured in 0.2-ml microwells in the presence of 3×10$^4$ Ag-pulsed APC. One day later, culture supernatants were harvested and tested at 50% concentration for their ability to support the proliferation of 10$^4$ HT-2 cells for 24 h (measured by incorporation of [3H] thymidine present during the final 6 h culture period).

TABLE 1

Exemplary Peptidic Sequences For Addition To Soluble Protein Antigens.

| Description | Designation |
|---|---|
| Cys-Lys-Lys-Lys-Lys-Lys-Lys-Lys-Lys-Lys-Lys-Lys-Lys-Lys-Lys-Lys-Lys-Lys-Lys | SEQ ID NO:1 (PK) |
| Cys-Glu-Ala-Ala-Ala-Ala-Ala-Glu-Ala-Ala-Ala-Ala-Ala-Glu-Ala-Ala-Ala-Ala-Ala-Glu-Ala-Ala-Ala-Ala-Ala-Ala | SEQ ID NO:2 (pEA) |
| Cys-Gly-Leu-Phe-Gly-Ala-Ile-Ala-Gly-Phe-Ile-Glu-Asn-Gly-Trp-Glu-Gly-Met-Ile-Asp-Gly-Trp-Tyr-Gly | SEQ ID NO:3 (HA) |
| Cys-Glu-Ala-Ala-Ala-Ala-Ala-Glu-Ala-Ala-Ala-Ala-Ala-Glu-Ala-Ala-Ala-Ala-Ala-Ala-Lys-Lys-Lys-Lys-Lys-Lys-Lys-Lys-Lys-Lys-Lys-Lys-Lys-Lys-Lys-Lys-Lys-Lys-Lys | SEQ ID NO:4 (tandem pEA/pK conjugate) |
| Cys-Gly-Leu-Phe-Gly-Ala-Ile-Ala-Gly-Phe-Ile-Glu-Asn-Gly-Trp-Glu-Gly-Met-Ile-Asp-Gly-Trp-Tyr-Gly-Lys-Lys-Lys-Lys-Lys-Lys-Lys-Lys-Lys-Lys-Lys-Lys-Lys-Lys-Lys-Lys-Lys-Lys-Lys | SEQ ID NO:5 (tandem HA/pK conjugate) |
| CYS-X-X-X-X-X-X-X-X-X-X-X-X-X-X-X-X-X-X, wherein X = arg or lys | SEQ ID NO:6 |
| X-X-X-X-X-X-X-X-X-X-X-X-X-X-X-X-X-X, wherein X = arg or lys | SEQ ID NO:7 |
| CYS-[X-Y-Y-Y-Y-Y]$_n$; wherein X = glu or asp, Y = ala, leu, ile, phe, gly, cys, met or val and n is greater than or equal to 3 | SEQ ID NO:8 |
| [X-Y-Y-Y-Y-Y]$_n$; wherein X = glu or asp, Y = ala, leu, ile, phe, gly, cys, met or val and n is greater than or equal to 3 | SEQ ID NO:9 |

Analysis of B3Z responses to EL-4 APC pre-pulsed with a wide range of antigen concentrations indicates that pEA/pK-conjugate of OVA is about 100 fold more efficient in stimulating B3Z than OVA itself. (See FIGS. 2A-C)

The above evidence appears to reflect improved penetration of pEA/pK-conjugated OVA into the class I-dependent Ag processing and presentation pathway. An additional experiment was conducted in order to eliminate the possibility that Ag-derived peptides in the conjugate (which do not require internalization or processing), were responsible for the observed improvement in B3Z responses. Cells were cultured as described above and EL-4 cells were fixed with 0.025% glutaraldehyde (Fluka, Buchs, Switzerland) prior to Ag pulsing. When APC were fixed with glutaraldehyde prior to Ag pulsing thereby preventing Ag internalization and processing, fixed EL-4 cells were observed to present the immunogenic peptide SIINFEKL to B3Z in a stimulatory fashion, while their capability to present OVA-pEA/pK was completely lost upon fixation (see FIG. 3). SIINFEKL (hereinafter SEQ ID NO: 10) is an OVA-derived peptide (OVA-$_{257-264}$), recognized by the T cell hybridoma B3Z. (Jameson et al., 1993, *J. Exp. Med.* 177: 1541). A residual (approximately 7%) B3Z response to fixed EL-4 pulsed with unmodified OVA was observed indicating that the latter, though 99% pure (Sigma, St. Louis, Mo.) may contain a minor fraction of degradation product(s), which are removed upon conjugation to pEA/pK.

EXAMPLE 2

Evaluation of in vivo Presentation of OVA-pEA/pK Conjugate

In general, T cell hybridomas represent highly activated memory T cells, with an activation threshold significantly lower then that required to trigger naive T cells (Ridge et al., 1998, *Nature* 393: 474). It has been found that only highly activated DC are capable of triggering effective CTL responses in animals not previously exposed to the antigen. Accordingly, we immunized virgin laboratory mice with Ag-pulsed DC in order to examine whether OVA conjugated to pK and pEA could elicit an effective CTL response.

Dendritic cells were pulsed by 16 h co-culture with either OVA (5 µM) or OVA-pEA/pK (0.5 µM), washed two times and injected into mice. Female C57BL/6 mice were either left untreated, or were immunized with two intraperitoneal (i.p.) injections of $5 \times 10^5$ Ag-pulsed cells in 0.1 ml phosphate buffered saline (PBS) at a two week interval. Two weeks after the last in vivo immunization, splenocytes were pooled from 2 mice of each group and restimulated in vitro by co-culturing them at a density of $4 \times 10^6$ cells/ml with gamma-irradiated (200 Gy) E.G7-OVA at $5 \times 10^5$ cells/ml, in the presence of the recombinant human IL-2 (10 u/ml; Genzyme, Cambridge, Mass.). Six days later the cultures were tested for their ability to lyse $^{51}$Cr-labeled E.G7-OVA and EL-4 target cells in a standard cell mediated cytotoxicity assay (Wunderlich and Shearer 1998, in Coligan et al. (eds.) *Current Protocols in Immunology Wiley*, New York, N.Y., 1:3.11).

Figure 4:
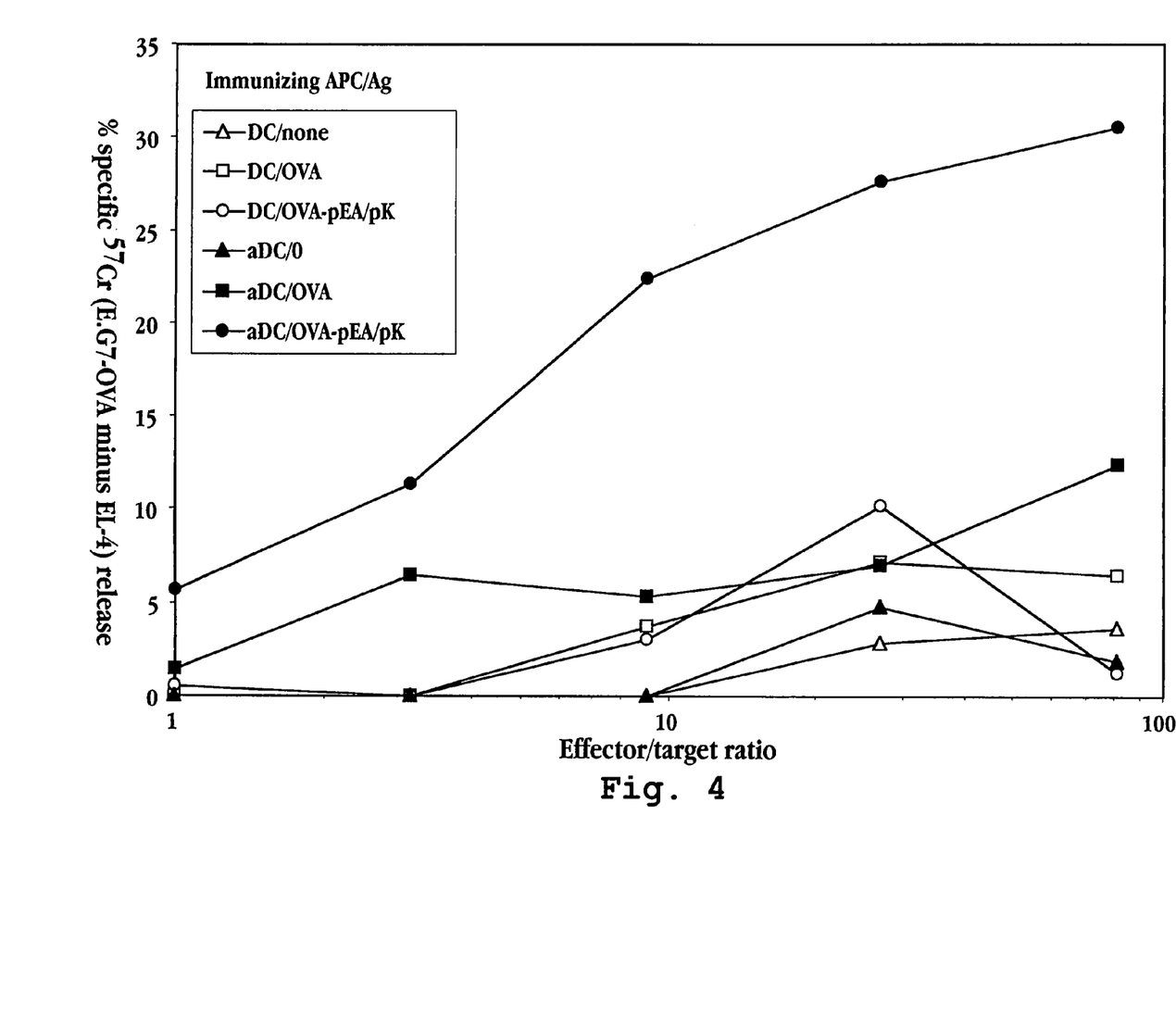
FIG. 4 shows the class I restricted OVA specific CTL responses of mice pre-immunized with Ag-pulsed DC. The enriched DC were prepared, pulsed with either OVA (5 μM) or OVA-pEA/pK (0.5 μM), and injected into mice as described in Example 2. Six days later the cultures were tested for their ability to lyse $^{51}$Cr-labeled E.G7-OVA and EL-4 target cells in a standard cell mediated cytotoxicity assay.

As shown in FIG. 4, only mice primed with DC previously pulsed with OVA conjugated to pEA and pK generated significant CTL responses against OVA-transfected target cells (E.G7-OVA), while the corresponding responses of mice immunized with OVA-pulsed DC were substantially lower.

Tumor specific CTL constitute an important effector limb of the anti-tumor immune response (Greenberg, 1991, *Adv. Immunol.* 49: 281). Accordingly, the effect of immunization with OVA-pEA/pK-pulsed DC on suppression of in vivo growth of OVA-expressing autologous tumors was evaluated.

Twenty 8-week old randomized female C57BL/6 mice were each injected i.p. with E.G7-OVA cells in 0.1 ml PBS (FIG. 5A: $25 \times 10^6$ cells per mouse; FIG. 5B: $2 \times 10^6$ cells per mouse). Two days and again 2 weeks later the mice received i.p. injections of either unpulsed DC, OVA-pulsed DC, OVA-pEA/pK-pulsed DC ($5 \times 10^5$ cells per 0.1 ml injection), or PBS. Mice were monitored daily and their survival was recorded.

As shown in FIG. 5, treatment with DC pulsed with OVA conjugated with pK and pEA exhibited a notable therapeutic effect, considerably prolonging the survival of tumor-bearing mice (statistical significance according to Student's t-test: p<0.01).

Although the invention has been described with reference to specific methods and embodiments, it will be appreciated that various modifications and changes may be made without departing from the invention.

What is claimed is:

1. A composition, comprising an antigen presenting cell (APC), stimulated by exposure "in vitro" to a modified antigen having an added peptidic sequence consisting of SEQ ID NO:2, wherein said stimulated APC is effective to activate T-cells to produce a cytotoxic cellular immune response against said antigen, at a T-cell activation level that is higher than that produced by such APC stimulated by the antigen alone.

2. The composition of claim 1, wherein said antigen is a soluble protein antigen.

3. The composition of claim 1, for use in immunizing a subject against a tumor or pathogen wherein said antigen is specific to the tumor or pathogen.

4. The composition of claim 1, wherein said added peptidic sequence is covalently linked to said antigen.

5. The composition of claim 1, wherein said antigen is a fusion protein produced by translation of a continuous nucleotide coding sequence.

* * * * *

SEQUENCE LISTING

<160> NUMBER OF SEQ ID NOS: 10

<210> SEQ ID NO 1
<211> LENGTH: 21
<212> TYPE: PRT
<213> ORGANISM: Artificial Sequence
<220> FEATURE:
<223> OTHER INFORMATION: pK

<400> SEQUENCE: 1

Cys Lys Lys Lys Lys Lys Lys Lys Lys Lys Lys Lys Lys Lys Lys Lys
1               5                   10                  15

Lys Lys Lys Lys Lys
            20

<210> SEQ ID NO 2
<211> LENGTH: 25
<212> TYPE: PRT
<213> ORGANISM: Artificial Sequence
<220> FEATURE:
<223> OTHER INFORMATION: pEA

<400> SEQUENCE: 2

Cys Glu Ala Ala Ala Ala Ala Glu Ala Ala Ala Ala Ala Glu Ala Ala
1               5                   10                  15

Ala Ala Ala Glu Ala Ala Ala Ala Ala
            20                  25

<210> SEQ ID NO 3
<211> LENGTH: 24

```
<212> TYPE: PRT
<213> ORGANISM: Artificial Sequence
<220> FEATURE:
<223> OTHER INFORMATION: HA

<400> SEQUENCE: 3

Cys Gly Leu Phe Gly Ala Ile Ala Gly Phe Ile Glu Asn Gly Trp Glu
 1               5                  10                  15

Gly Met Ile Asp Gly Trp Tyr Gly
            20

<210> SEQ ID NO 4
<211> LENGTH: 45
<212> TYPE: PRT
<213> ORGANISM: Artificial Sequence
<220> FEATURE:
<223> OTHER INFORMATION: tandem pEA/pK conjugate

<400> SEQUENCE: 4

Cys Glu Ala Ala Ala Ala Ala Glu Ala Ala Ala Ala Glu Ala Ala
 1               5                  10                  15

Ala Ala Ala Glu Ala Ala Ala Ala Ala Lys Lys Lys Lys Lys Lys
            20                  25                  30

Lys Lys Lys Lys Lys Lys Lys Lys Lys Lys Lys Lys
        35                  40                  45

<210> SEQ ID NO 5
<211> LENGTH: 44
<212> TYPE: PRT
<213> ORGANISM: Artificial Sequence
<220> FEATURE:
<223> OTHER INFORMATION: tandem HA/pK conjugate

<400> SEQUENCE: 5

Cys Gly Leu Phe Gly Ala Ile Ala Gly Phe Ile Glu Asn Gly Trp Glu
 1               5                  10                  15

Gly Met Ile Asp Gly Trp Tyr Gly Lys Lys Lys Lys Lys Lys Lys
            20                  25                  30

Lys Lys Lys Lys Lys Lys Lys Lys Lys Lys Lys Lys
        35                  40

<210> SEQ ID NO 6
<211> LENGTH: 21
<212> TYPE: PRT
<213> ORGANISM: Artificial Sequence
<220> FEATURE:
<223> OTHER INFORMATION: added peptidic sequence with a combination of
      lys and arg residues, with an N-terminal cys residue
<220> FEATURE:
<221> NAME/KEY: VARIANT
<222> LOCATION: (1)...(21)
<223> OTHER INFORMATION: Xaa = Arg or Lys

<400> SEQUENCE: 6

Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa
            20

<210> SEQ ID NO 7
<211> LENGTH: 20
<212> TYPE: PRT
<213> ORGANISM: Artificial Sequence
```

```
<220> FEATURE:
<223> OTHER INFORMATION: added peptidic sequence with a combination of
      lys and arg residues
<220> FEATURE:
<221> NAME/KEY: VARIANT
<222> LOCATION: (1)...(20)
<223> OTHER INFORMATION: Xaa = Arg or Lys

<400> SEQUENCE: 7

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa
            20

<210> SEQ ID NO 8
<211> LENGTH: 7
<212> TYPE: PRT
<213> ORGANISM: Artificial Sequence
<220> FEATURE:
<223> OTHER INFORMATION: peptidic sequence with repeating subunits,
      with an N-terminal cys residue
<220> FEATURE:
<221> NAME/KEY: VARIANT
<222> LOCATION: (2)...(2)
<223> OTHER INFORMATION: Xaa = Glu or Asp
<220> FEATURE:
<221> NAME/KEY: VARIANT
<222> LOCATION: (3)...(7)
<223> OTHER INFORMATION: Xaa = Ala, Leu, Ile, Phe, Gly, Cys, Met or Val
<220> FEATURE:
<221> NAME/KEY: VARIANT
<222> LOCATION: (2)...(7)
<223> OTHER INFORMATION: amino acids 2 to 7 comprise a subunit that is
      repeated three or more times

<400> SEQUENCE: 8

Cys Xaa Xaa Xaa Xaa Xaa Xaa
 1               5

<210> SEQ ID NO 9
<211> LENGTH: 6
<212> TYPE: PRT
<213> ORGANISM: Artificial Sequence
<220> FEATURE:
<223> OTHER INFORMATION: peptidic sequence with repeating subunits
<220> FEATURE:
<221> NAME/KEY: VARIANT
<222> LOCATION: (1)...(1)
<223> OTHER INFORMATION: Xaa = Glu or Asp
<220> FEATURE:
<221> NAME/KEY: VARIANT
<222> LOCATION: (2)...(6)
<223> OTHER INFORMATION: Xaa = Ala, Leu, Ile, Phe, Gly, Cys, Met or Val
<220> FEATURE:
<221> NAME/KEY: VARIANT
<222> LOCATION: (1)...(6)
<223> OTHER INFORMATION: amino acids 1 to 6 comprise a subunit that is
      repeated three or more times

<400> SEQUENCE: 9

Xaa Xaa Xaa Xaa Xaa Xaa
 1               5

<210> SEQ ID NO 10
<211> LENGTH: 8
<212> TYPE: PRT
<213> ORGANISM: Artificial Sequence
<220> FEATURE:
```

```
-continued

<223> OTHER INFORMATION: OVA- derived peptide (OVA 257-264),
      recognized by the T cell hybridoma B3Z. (Jameson et al., 1993, J.
      Exp. Med. 177: 1541)

<400> SEQUENCE: 10

Ser Ile Ile Asn Phe Glu Lys Leu
  1               5
```